United States Patent [19]
Kanji et al.

[11] Patent Number: 5,292,963
[45] Date of Patent: Mar. 8, 1994

[54] PROCESS FOR PRODUCING ETHER COMPOUND

[75] Inventors: Nakagawa Kanji; Matsuo Makoto, both of Ichihara, Japan

[73] Assignee: UBE Industries, Ltd., Yamaguchi, Japan

[21] Appl. No.: 962,264

[22] Filed: Oct. 16, 1992

[30] Foreign Application Priority Data

Oct. 18, 1991 [JP] Japan .................. 3-333836

[51] Int. Cl.$^5$ .............................................. C07C 41/06
[52] U.S. Cl. ................................. 568/697; 568/699
[58] Field of Search ............................ 568/697, 699

[56] References Cited

U.S. PATENT DOCUMENTS

| | | | |
|---|---|---|---|
| 3,726,942 | 4/1973 | Louder ........................... | 568/697 |
| 4,302,298 | 11/1981 | Mikitenko et al. . | |
| 4,378,324 | 3/1983 | Makino et al. . | |
| 4,447,653 | 5/1984 | Vora . | |
| 4,544,776 | 10/1985 | Osterburg et al. . | |
| 4,605,787 | 8/1986 | Chu et al. . | |
| 4,690,873 | 9/1987 | Makino et al. . | |
| 4,774,365 | 9/1988 | Chen et al. . | |
| 4,959,151 | 9/1990 | Nakatani et al. . | |

FOREIGN PATENT DOCUMENTS 2242429  10/1991  United Kingdom .

OTHER PUBLICATIONS

Aiche, Symposium Series, 85 (272), 82(1989).

*Primary Examiner*—Howard T. Mars
*Attorney, Agent, or Firm*—Burgess, Ryan & Wayne

[57] ABSTRACT

An ether compound is continuously produced by a process in which (1) a $C_{1-3}$ lower alcohol is reacted with a $C_{3-6}$ hydrocarbon mixture comprising, as the major component thereof, an unsaturated $C_{4-5}$ hydrocarbon compound; (2) the resultant mixture comprising the ether compound, a non-reacted lower alcohol and a non-reacted hydrocarbon mixture is distilled to provide a bottom liquid fraction comprising the ether compound and a top vapor fraction comprising the non-reacted lower alcohol and hydrocarbon mixture; (3) the bottom liquid fraction is collected (4) the top vapor fraction discharged through a top outlet of the distillation column and liquefied is fed to a separating membrane module whereby the liquefied top fraction is brought into contact with one side face of an aromatic polyimide asymmetric separating membrane having a separation factor, of 200 or more, while exposing the opposite side face of the membrane to a reduced pressure so as to allow the lower alcohol fraction to selectively permeate, through the membrane; and (5) the permeated lower alcohol fraction is cooled and returned to the reaction step.

15 Claims, 1 Drawing Sheet

PROCESS FOR PRODUCING ETHER COMPOUND

BACKGROUND OF THE INVENTION

1. Field of the Invention

The present invention relates to a process for producing an ether compound. More particularly, the present invention relates to a process for producing an ether compound, for example, methyl-tert-butyl ether, by reacting a lower alcohol, for example, methyl alcohol, with a hydrocarbon mixture comprising, as the major component thereof, an unsaturated hydrocarbon compound, for example, isobutylene; subjecting the resultant reaction product mixture comprising the resultant ether compound and non-reacted portions of the lower alcohol and hydrocarbon mixture to a distillation to provide a distillation vapor fraction comprising the non-reacted lower alcohol and hydrocarbon mixture and a liquid fraction comprising the resultant ether compound that is collected from the distillation step; selectively recovering the non-reacted lower alcohol from the distillation vapor fraction by using a specific aromatic polyimide asymmetric separating membrane; and returning the recovered non-reacted lower alcohol to the reaction step.

Namely, in the process of the present invention, the reaction product mixture obtained from the reaction step is subjected to a distillation procedure in a distillation column, for example, a multi-pass distillation column to provide a distillation vapor fraction comprising the non-reacted lower alcohol and hydrocarbon mixture, which is collected through a top outlet of the distillation column and a liquid fraction comprising the resultant ether compound, which is recovered through a bottom outlet of the distillation column. The collected distillation vapor fraction is subjected to a pervaporation procedure in which a specific asymmetric separating membrane is employed and the non-reacted lower alcohol is selectively recovered with a high degree of purity and high efficiency by permeating through the separating membrane. The recovered vapor fraction comprising, as the major component thereof, the non-reacted lower alcohol is liquefied by cooling and then returned to the reaction step, to recyclically use the lower alcohol.

2. Description of the Related Art

It is known that an ether compound, for example, methyl-tert-butyl-ether, is produced by reacting a $C_4$ petroleum fraction (hydrocarbon mixture) containing an unsaturated hydrocarbon compound, for example, isobutylene, with an excess amount of a lower alcohol, for example, methyl alcohol, as disclosed in U.S. Pat. Nos. 4,302,298, 4,447,653, 4,544,776, 4,605,787 and 4,774,365.

In this conventional process, the resultant reaction product mixture comprises the resultant reaction product, namely an ether compound, a non-reacted portion of the lower alcohol and a non-reacted portion of the unsaturated hydrocarbon compound.

A conventional process for recovering and refining the resultant ether compound and the non-reacted reactant compounds comprises a complicated combination of one or more distillation steps and one or more extraction steps. For example, the conventional process is carried out by employing a reaction column in which the lower alcohol is reacted with the hydrocarbon mixture, a distillation column in which non-reacted compounds are separated from each other and recovered, a water-washing column in which the distillation vapor fraction generated in the distillation column comprising the non-reacted lower alcohol is washed with water to extract the non-reacted lower alcohol in water, and a dehydration column in which the non-reacted lower alcohol is recovered by removing water from the lower alcohol-containing water extract.

The reaction of the lower alcohol with the unsaturated hydrocarbon compound is carried out in accordance with an equilibrium reaction theory, and therefore, the lower alcohol must be employed in an excessive amount to enhance the conversion of the unsaturated hydrocarbon compound. Therefore, after completion of the reaction, a large amount of non-reacted lower alcohol remains in the reaction product mixture. This non-reacted lower alcohol must be recovered from the resultant reaction product mixture.

When the recovery of the non-reacted lower alcohol is carried out by a conventional distillation procedure, an excessively large load needs to be applied to the recovery process and therefore the recovering (refining) apparatus becomes large and a large amount of energy for carrying out the recovering (refining) process is consumed.

AICHE Symposium Series, 85 (272), 82 (1989) discloses a process for producing methyl-tert-butylether, in which methyl alcohol is reacted with isobutylene to produce methyl-tert-butylether (MTBE); the resultant reaction product mixture is subjected to a pervaporation procedure using a separating membrane made of a cellulose acetate so as to recover a vapor fraction permeated through the separating membrane and comprising non-reacted portion of methyl alcohol, and a liquid fraction not permeated through the separating membrane; the permeated vapor fraction is returned to the reaction. step; the non-permeated liquid fraction is fed to a distillation-extraction process so as to separate the non-reacted isobutylene portion from the reaction product.

In the above-mentioned process, the cellulose acetate separating membrane exhibits a relatively low separation factor ($CH_3OH/MTBE$) of 5 to 20 and a relatively low separation factor ($CH_3OH/C_4$-fraction) of 1 to 3. Accordingly, it is difficult to recover the non-reacted methyl alcohol with a high degree of purity. Also, the non-permeated liquid fraction collected in a feed side of the separating membrane contains a certain amount of non-reacted methyl alcohol together with the resultant MTBE and the non-reacted isobutylene. Accordingly, it is difficult to recover the non-reacted methyl alcohol with high efficiency, unless the non-permeated liquid fraction is subjected to a distillation process, water-washing and dehydrating procedures similar to those of the above-mentioned conventional process.

Accordingly, the above-mentioned conventional processes are not satisfactory for practical use.

SUMMARY OF THE INVENTION

An object of the present invention is to provide a process for producing an ether compound by a reaction of a lower alcohol with a hydrocarbon mixture comprising the major component thereof, an unsaturated hydrocarbon compound with a reduced energy consumption for recovering a reaction product and non-reacted portions of the lower alcohol and hydrocarbon mixture.

Another object of the present invention is to provide a process for producing an ether compound with a high level of efficiency by easy and simplified procedures.

The above-mentioned objects can be attained by the process of the present invention for producing an ether compound, which comprises the steps of:

subjecting a lower alcohol having 1 to 3 carbon atoms to a reaction procedure with a hydrocarbon mixture consisting of hydrocarbon compounds having 3 to 6 carbon atoms and comprising, as the major component thereof, an unsaturated hydrocarbon compound having 4 or 5 carbon atoms, to provide a reaction product mixture comprising a resultant ether compound, a non-reacted portion of the lower alcohol and a non-reacted portion of the hydrocarbon mixture;

feeding the resultant reaction product mixture to a distillation procedure in a distillation column, to provide a bottom liquid fraction comprising the resultant ether compound and a top vapor fraction comprising the non-reacted lower alcohol portion and the non-reacted hydrocarbon mixture portion;

collecting the bottom liquid fraction through a bottom outlet of the distillation column;

discharging the top vapor fraction through a top outlet of the distillation column;

liquefying the top vapor fraction by cooling;

bringing the liquefied top fraction into contact with one side face of an aromatic polyimide asymmetric separating membrane having a separation factor as defined below, of 200 or more, at a temperature of 50° C. or more, while exposing the opposite side face of the separating membrane to an atmosphere maintained under a reduced pressure, to allow a vapor fraction comprising as a major component thereof, the non-reacted lower alcohol to selectively permeate through the separating membrane, the separation factor being determined in accordance with the equation $$\alpha = C_1/C_2$$

wherein $\alpha$ represents the separation factor of the separating membrane, $C_1$ represents a proportion in weight of the non-reacted lower alcohol contained in the permeated fraction to the non-reacted hydrocarbon mixture contained in the permeated fraction and $C_2$ represents a proportion in weight of the non-reacted lower alcohol contained in the liquefied top fraction to the non-reacted hydrocarbon mixture contained in the liquefied top fraction;

cooling the permeated lower alcohol vapor fraction to liquefy and collect the same;

returning the liquefied lower alcohol fraction to the reaction step.

DESCRIPTION OF THE PREFERRED EMBODIMENTS

Figure 1:
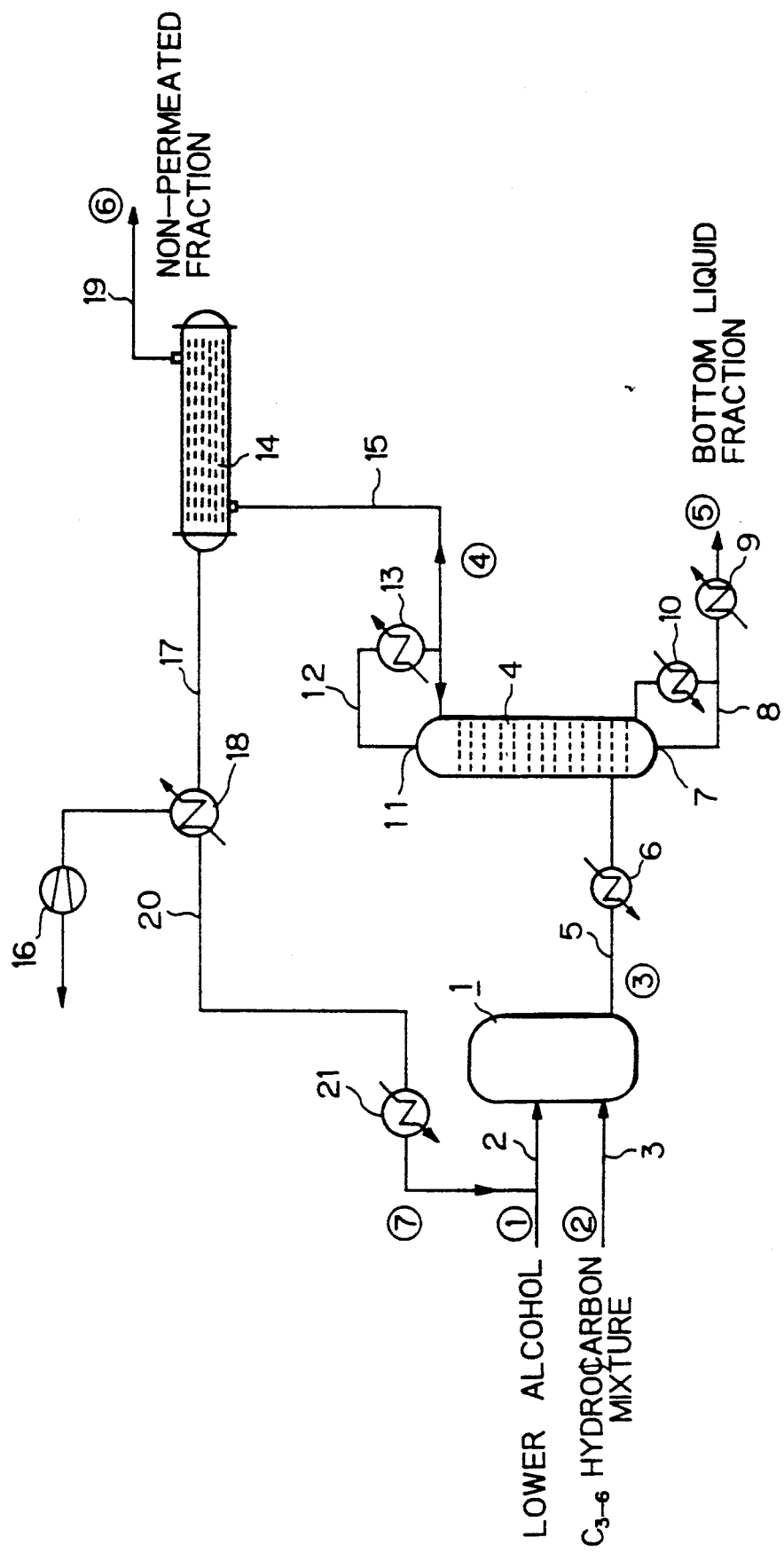
FIG. 1 is a diagram showing a process system usable for carrying out the process of the present invention.

The process of the present invention is carried out, for example, by a process system as shown in FIG. 1.

Referring to FIG. 1, a lower alcohol having 1 to 3 carbon atoms is fed into a reaction column 1 through a conduit 2, and a hydrocarbon mixture consisting of hydrocarbon compounds having 3 to 6 carbon atoms and comprising, as the major component thereof, an unsaturated hydrocarbon compound having 4 or 5 carbon atoms, is fed into the reaction column 1 through a conduit 3. The lower alcohol reacts with the unsaturated hydrocarbon compound in the reaction column 1 to provide an ether compound.

In the process of the present invention, the lower alcohol having 1 to 3 carbon atoms is preferably selected from the group consisting of methyl alcohol, ethyl alcohol and propyl alcohol. The most preferable lower alcohol for the process of the present invention is methyl alcohol.

In the process of the present invention, the unsaturated hydrocarbon compound having 4 or 5 carbon atoms is preferably selected from the group consisting of isobutylene, 2-methyl-2-butene and 2-methyl-1-butene. The most preferable unsaturated hydrocarbon compounds for the process of the present invention are isobutylene and 2-methyl-2-butene.

The hydrocarbon mixture usable for the process of the present invention consists of hydrocarbons having 3 to 6 carbon atoms, whose mixture is referred to as a $C_{3-6}$ petroleum fraction, and comprises an unsaturated hydrocarbon compound having 4 or 5 carbon atoms, preferably in an amount of 10 to 80%, more preferably 20 to 50%, based on the total weight of the hydrocarbon mixture.

Usually, the reaction step of the lower alcohol with the unsaturated hydrocarbon mixture is carried out in a liquid phase at a temperature of from 30° C. to 100° C. under a pressure of from 5 to 30 kg/cm² G.

Preferably, the resultant reaction product mixture comprises 20 to 75% by weight of a reaction product (ether compound), 0.5 to 10% by weight of non-reacted portion of the lower alcohol, and 25 to 80% by weight of non-reacted portion of the $C_{3-6}$ hydrocarbon mixture.

For example, when a $C_4$ petroleum fraction containing isobutylene and methyl alcohol in a slightly excess amount is fed to the reaction column, the reaction step is carried out at a temperature of from 30° C. to 100° C., preferably 40° C. to 90° C., under a pressure of 2 to 16 kg/cm² G, preferably 4 to 15 kg/cm². Preferably, the reaction is effected in the presence of a catalyst consisting of, for example, a strong acid ion exchange resin. In this case, the $C_4$ petroleum fraction preferably contains isobutylene in an amount of 10 to 60% by weight. Also, the resultant MTBE-containing a reaction mixture preferably comprises 25 to 75% by weight of MTBE, 0.5 to 10% by weight of non-reacted methyl alcohol and 30 to 75% by weight of non-reacted $C_4$ hydrocarbon mixture.

Referring to FIG. 1, the reaction product mixture withdrawn from the reaction column 1 and fed to a distillation column 4 through a conduit 5 and optionally a heater 6. The reaction product mixture preferably has a temperature of 30 to 100° C. If necessary, the reaction product mixture is heated to the above-mentioned temperature by using the heater 6.

In the distillation procedure in the distillation column 4, the reaction product mixture is divided into a bottom liquid fraction containing, as the major component thereof, the resultant ether compound, and a top vapor fraction comprising, as the major component thereof, the non-reacted portions of the lower alcohol and hydrocarbon mixture.

The bottom liquid fraction is recovered from the distillation column 4 through a bottom outlet 7, a conduit 8 and a cooler 9. Optionally, a heater 10 is arranged between the bottom of the distillation column 4 and the cooler 9, to heat the recovered liquid fraction and return same to the distillation column 4.

The top vapor fraction is withdrawn through a top outlet 11 of the distillation column 4 and a conduit 12, and the withdrawn top vapor fraction is liquefied by a cooler 13.

Then, the liquefied top fraction is fed to a separating membrane module 14 through a conduit 15.

The separating membrane module 14 contains therein at least one separating aromatic polyimide asymmetric membrane having a separation factor of 200 or more, preferably 400 to 10,000.

The separation factor is determined in accordance with the equation $$\alpha = C_1/C_2$$

wherein α represents the separation factor of the separating membrane, $C_1$ represents a proportion in weight of the non-reacted lower alcohol in the permeated fraction to the non-reacted hydrocarbon mixture in the permeated fraction and $C_2$ represents a proportion in weight of the non-reacted lower alcohol in the liquefied top fraction to the non-reacted hydrocarbon mixture in the liquefied top fraction.

The liquefied top fraction is brought into contact with one side face of the separating membrane at a temperature of 40° C. to 100° C., while exposing the opposite side face of the separating membrane to an atmosphere maintained under reduced pressure, for example, 200 Torr or less.

In the separating membrane module, a fraction comprising, as the major component, the non-reacted lower alcohol is allowed to selectively permeate in the state of a vapor the separating membrane.

Referring to FIG. 1, the feed side of the separating membrane module 14 is connected to the top outlet 11 of the distillation column 4 and the opposite (delivery) side of the separating membrane module 14 is connected to a vacuum pump 16 through a conduit 17 and a cooler 18. A fraction not permeated through the separating membrane is withdrawn from the feed side of the separating membrane module 14 through a conduit 19. The permeated fraction is withdrawn from the opposite side of the module 14 and cooled and liquefied by the cooler 18.

The liquefied fraction is returned to the reaction column 1 through a conduit 20 and optionally a heater 21. If necessary, the liquefied fraction is heated at a desired temperature and then returned to the reaction column 1 and subjected to the reaction step in the reaction column 1. When a top vapor fraction derived from a reaction procedure of methyl alcohol with the $C_{3-6}$ hydrocarbon mixture is fed to aromatic polyimide asymmetric separating membrane, the methyl alcohol permeates the membrane at a permeation rate of about 0.1 kg/m²·hr or more, preferably 0.2 to 7 kg/m²·hr. Also, the aromatic polyimide asymmetric separating membrane exhibits a separation factor, as defined above, of 200 or more.

The aromatic polyimide for the asymmetric separating membrane preferably comprises 70 to 100 molar %, more preferably 80 to 100 molar %, of at least one type of recurring units selected from those of the formulae (I) and (II):

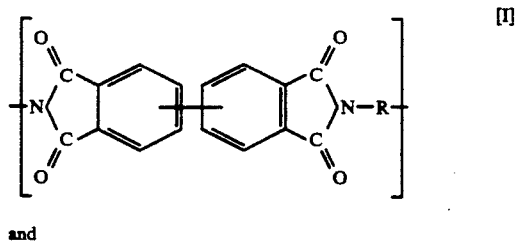

and

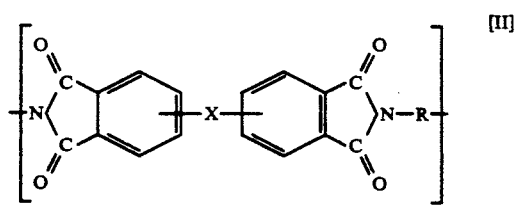

wherein R represents a divalent aromatic group having 2 to 4 benzene ring structures and X represents a member selected from the group consisting of —S—, —SO₂—, —CO—, —O—, —C(CH₃)₂—, —CH₂—, and —C(CF₃)₂— groups.

The aromatic polyimide optionally comprises 0 to 30 molar %, more preferably 0 to 20 molar % of additional recurring imide units different from those of the formulae (I) and (II).

The additional recurring imide units may be derived from a polymerization reaction of an aromatic tetracarboxylic acid such as pyromellitic acid with an aromatic diamine compound selected from, for example, diaminodiphenylether, diaminodiphenylsulfone, diaminodiphenylenesulfone, diaminothioxantones, and diaminothioxanthenes.

The aromatic polyimide usable for the present invention is preferably solvent soluble and comprises a polymerization product of:

(A) an aromatic tetracarboxylic acid component comprisincy (a) 70 to 100 molar %, more preferably 80 to 100 molar %, of at least one principal aromatic tetracarboxylic acid compound selected from the group consisting of biphenyltetracarboxylic acids, diphenylthioether tetracarboxylic acids, diphenylether tetracarboxylic acids, benzophenone tetracarboxylic acids, diphenylsulfone tetracarboxylic acids, diphenylthioether tetracarboxylic acids, diphenylhexafluoropropane tetracarboxylic acids and dianhydrides, esters and salts of the above-mentioned acids, and (b) 0 to 30 molar %, more preferably, 0 to 20 molar %, of at least one additional aromatic tetracarboxylic acid compound selected from the group consisting of aromatic tetracarboxylic acids different from the above-mentioned principal aromatic tetracarboxylic acids (a), dianhydrides, esters and salts of the above-mentioned acids; with (B) an aromatic diamine components comprising (c) 70 to 100 molar %, more preferably 80 to 100 molar %, of at least one principal aromatic diamine compound having 2 to 4 benzene ring structure, and (d) 0 to 30 molar %, more preferably 0 to 20 molar %, of at least one additional aromatic diamine compound different from the above-mentioned principal aromatic diamine compound (c).

The recurring units of the formula (I) are derived from a biphenyltetracarboxylic acid component and an aromatic diamine compound having 2 to 4 benzene ring structures.

Also, the recurring units of the formula (II) is derived from a member selected from the group consisting of diphenylethertetracarboxylic acid compounds, benzophenonetetracarboxylic acid compounds, diphenylsulfonetetracarboxylic acid compounds, diphenylpropanetetracarboxylic acid compounds, diphenylthioethertetracarboxylic acid comounds, diphenylhexafluoropropanetetracarboxylic acid compounds and diphenylmethanetetracarboxylic acid compounds, and an aromatic diamine compound having 2 to 4 benzene ring structures.

In the aromatic tetracarboxylic acid component (A), the principal aromatic tetracarboxylic acid compound (a) is preferably selected from the group consisting of 2,3,3',4'-biphenyltetracarboxylic acid, 3,3',4,4'-biphenyltetracarboxylic acid, 3,3',4,4'-diphenylether tetracarboxylic acid, 3,3',4,4'-benzophenonetetracarboxylic acid, 3,3',4,4'-diphenylthioethertetracarboxylic acid, 3,3',4,4'-diphenylsulfonetetracarboxylic acid, 2,2-bis(3,4-carboxyphenyl)propane, and 2,2-bis(3,4-carboxyphenyl)hexafluoropropane, and dianhydrides, acid chlorides and lower alkyl esters of the above-mentioned acids.

Most preferable principal aromatic tetracarboxylic acid compounds are 3,3',4,4'-biphenyltetracarboxylic dianhydride and 3,3'4,4'-diphenylethertetracarboxylic dianhydride. Those tetracarboxylic dianhydrides have excellent polymerization properties for the polyimide, asymmetric membrane-forming properties for the separating membrane, separating properties for the lower alcohol from the hydrocarbon mixture, and polymer-forming properties for a polyimide having superior durability, mechanical strength and heat-resistance.

The additional aromatic tetracarboxylic acid compound (b) is preferably selected from the group consisting of pyromellitic acid, 3,4,9,10-perylenetetracarboxylic acid and 1,4,5,8-naphthalenetetracarboxylic acid and dianhydrides acid chlorides and lower esters of the above-mentioned acids.

The principal aromatic diamine compound (c) is preferably selected from the group consisting of aromatic diamine compounds having two-benzene ring structures, for example, diaminodiphenylethers, diaminodiphenylthioethers, diaminodiphenylsulfones, diaminodiphenylmethanes, diaminodiphenyl propanes, diaminodibenzothiophenes, diaminodiphenylenesulfones, diaminothioxanthones, and diaminothioxanthenes; aromatic diamine compounds having 3 benzene ring structures, for example, bis(aminophenoxy)benzenes, and di(aminophenyl)benzenes; aromatic diamine compounds having 4 benzene ring structures, for example, di[(aminophenoxy)phenyl]alkanes, di[(aminophenoxy)phenyl]sulfones, and di(aminophenoxy)biphenyls; and 9,10-(diaminophenyl)anthracene compounds.

The aromatic diamine compounds having 2 benzene ring structures are preferably selected from the group consisting of 4,4'-diaminodiphenylether, 3,4'-diaminodiphenylether, 4,4'-diaminodiphenylmethane, 3,3'-dimethyl-4,4'-diaminodiphenylmethane, 2,2-bis(4-aminophenyl)propane, 2,2-bis(3-aminophenyl)propane, 4,4'-diaminophenylsulfone, 3,3'-diaminodiphenylsulfone, o-, and m-dianisidines, and the aromatic diamine compounds of the formulae (III) and (IV):

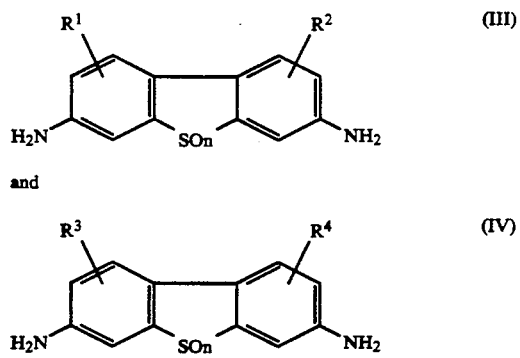

in which formulae (III) and (IV), $R^1$, $R^2$, $R^3$ and $R^4$ respectively and independently represent a member selected from the group consisting of a hydrogen atom and a methyl radical, and n is zero or an integer of 2.

The diamine compounds of the above-mentioned formula (III) are preferably selected from the group consisting of diaminodibenzothiophene compounds, for example, 3,7-diaminodibenzothiophene, 2,8-dimethyl-3,7-diaminodibenzothiophene, and 2,8-diethyl-3,7-diaminodibenzothiophene; and diaminodibenzothiophene-5,5-dioxide compounds (namely diaminodiphenylenesulfone compounds), for example, 3,7-diaminodibenzothiophene-5,5-dioxide, 2,8-dimethyl-3,7-diaminodibenzothiophene-5,5-dioxide and 2,8-diethyl-3,7-diaminodibenzothiophene-5,5-dioxide.

The diamine compounds of the above-mentioned formula (IV) are preferably selected from the group consisting of diaminothioxanthene compounds, for example, 3,7-diaminothioxanthene and 2,8-dimethyl-3,7-diaminothioxanthene; and diaminothioxanthene-5,5-dioxide compounds, for example, 3,7-diaminothioxanthene-5,5-dioxide and 2,8-dimethyl-3,7-diaminothioxanthene-5,5-dioxide.

The aromatic diamine compounds having 3 benzene ring structures are preferably selected from the group consisting of bis(aminophenoxy)benzene compounds, for example, 1,4-bis(4-aminophenoxy)benzene, 1,4-bis(3-aminophenoxy)benzene, 1,3-bis(4-aminophenoxy)benzene.

The 9,10-di(aminophenyl)anthracene compounds include 9,10-bis(4-aminophenyl)anthracene, 9,10-bis(3-aminophenyl)anthracene and 9-(4-aminophenyl)-10-(3-aminophenyl)anthracene.

During the preparation of the aromatic polyimide, the aromatic diamine compound having 2 or more benzene ring structures can be employed together with m- or p-phenylenediamine in a small amount of 10 molar % or less and at least one member selected from diaminobenzoic acid compounds and alkylphenyldiamine compounds in a minor amount of 30 molar % or less.

The asymmetric separating membrane usable for the process of the present invention can be prepared from an aromatic polyimide in accordance with a wet membrane-forming processes as described in U.S. Pat. No. 4,378,324. In this wet membrane-forming process, a dope solution of an aromatic polyimide in phenolic solvent in a polymer concentration of 5 to 30% by weight is formed into a thin layer, for example, in the form of a flat film or a hollow filament, by a solution-spreading method, solution-extruding method or hollow filament-spinning method, and the thin solution layer is brought into contact with a coagulation liquid at a relatively low temperature to solidify the thin solution layer and to provide an asymmetric aromatic polyimide membrane in the form of a thin flat film or a hollow filament.

Preferably, the asymmetric separating membrane prepared by the above-mentioned wet membrane-forming method is washed with methyl alcohol, ethyl alcohol, n-hexane, or cyclohexane, fully dried and then subjected to a heat treatment or aging treatment in a gas atmosphere comprising nitrogen or air at a temperature of from about 150° C. to about 400° C. for a time of from one second to 20 hours.

The aromatic polyimide asymmetric separating membrane usable for the process of the present invention is preferably in the form of a flat film or a hollow filament having a thickness of from 10 to 2,000 μm. The asymmetric separating membrane preferably comprises a dense layer having a thickness of about 0.001 to about 5 μm and a porous layer having a thickness of about 10 to about 2,000 μm and continuing from the dense layer in the direction of the thickness of the membrane.

In the process of the present invention as shown in FIG. 1, the step for recovering the non-reacted lower alcohol from the liquefied top fraction by using the separating membrane module 4, comprises the operations of:

(a) directly feeding the liquefied top fraction into the separating membrane module 4 containing one or more aromatic polyimide asymmetric separating membranes in the form of a flat film or hollow filament, so that the liquefied top fraction comes into contact with a feed side face of the each separating membrane, (b) allowing a fraction comprising, as the major component thereof, the non-reacted low alcohol to selectively permeate in the state of a vapor the asymmetric separating membrane by reducing the pressure on the opposite side (delivery side) of the asymmetric separating membrane and optionally flowing a carrier (sweeping) gas through the opposite (delivery) side by driving the vacuum pump 16;

(c) recovering a non-permeated liquid fraction remaining in the feed side of the separating membrane, and comprising the non-reacted hydrocarbon mixture in an increased concentration, from the separating membrane module 14 through the conduit 19, and simultaneously recovering the permeated vapor fraction comprising the lower alcohol in an increased concentration from the opposite (delivery) side of the separating membrane through the conduit 17;

(d) cooling the permeated vapor fraction to a temperature of 30° C. or less by the cooler 18 to condense and liquefy the vapor fraction.

In the process of the present invention, the liquefied top fraction is fed at a temperature of 50° C. or more, preferably 50° C. to 100° C., more preferably 60° C. to 80° C., to the separating membrane module 14.

Also, in the non-reacted lower alcohol-separating step in the separating membrane module, the pressure on the opposite (delivery) side must be lower than that on the feed side of the separating membrane. The liquefied top fraction is fed under a pressure of from ambient atmospheric pressure to 20 kg/cm², preferably from ambient atmospheric pressure to 10 kg/cm², to the feed side of the separating membrane.

Also, in the lower alcohol-separating step, the opposite (delivery) side of the separating membrane is under a pressure lower than that on the feed side and optionally, a sweep gas is forced through the opposite side of the separating membrane to collect the permeated vapor fraction.

The pressure on the opposite side of the separating membrane is preferably lower than that of the ambient atmospheric pressure, more preferably 200 Torr or less, and still more preferably 100 Torr or less.

In the process of the present invention, the non-reacted lower alcohol can be selectively separated and recovered from the liquefied top fraction by a pervaporation procedure in which the non-reacted lower alcohol-containing-fraction is selectively forced, in the state of a vapor, through an aromatic polyimide asymmetric separating membrane having a specific permeability ratio and the permeated vapor fraction is collected in the delivery side of the separating membrane.

Also, the non-reacted hydrocarbon mixture is separated from the non-reacted lower alcohol and collected in the feed side of the separating membrane.

The recovered hydrocarbon mixture is free from water. Therefore, when used for a alkylation procedure, the recovered hydrocarbon mixture does not deactivate a catalyst for the alkylation reaction and thus can be used for the alkylation procedure without any pretreatment.

In the process of the present invention, the distillation procedure can be carried out by feeding a reaction product mixture withdrawn from a reaction column 1 as shown in FIG. 1 into a distillation column 4, for example, having a plurality of flow-regulating plates arranged therein. Referring to FIG. 1, a cooler 13 is connected to a top portion of the distillation column 4, and a heater 10 is connected to a bottom portion of the distillation column 4. The distillation procedure is carried out under conditions such that the non-reacted lower alcohol and the hydrocarbon mixture containing the non-reacted unsaturated hydrocarbon compound are distilled to provide a top vapor fraction which is collected through a top outlet 11 of the distillation column 4 and then liquefied by cooling, and the resultant ether compound remains as a bottom liquid fraction, which is recovered through a bottom outlet 7 of the distillation column 4.

The process of the present invention can be applied to a production of methyl-tert-butylether, 2-ethoxy-2-methylpropane, 2-propoxy-2-methylpropane, 2-methoxy-2-methylbutane, or 2-ethoxy-2-methylbutane.

EXAMPLES

The present invention will be further illustrated by way of a specific example, which are merely representative and do not restrict the scope of the present invention in any way.

In the example, a separating membrane module was prepared in such a manner that four aromatic polyimide hollow filaments were bundled to form a hollow filament bundle, an end of the bundle was sealed with an epoxy resin, and then the resultant hollow filamentary separating membrane element was placed in a closed container. The container had an inlet for feeding a mixture of a lower alcohol with a hydrocarbon mixture into one side (feed side) of the separating membrane element, an outlet for discharging a non-permeated liquid fraction from the feed side of the separating membrane element, and an outlet for discharging a permeated fraction from the opposite (delivery) side of the separating membrane element.

In the example, a permeation rate of methyl alcohol through the separating membrane and a separation factor of the separating membrane for methyl alcohol and a $C_4$ hydrocarbon compound were determined in the following manner.

A feed mixture of 5% by weight of methyl alcohol with 95% by weight of a hydrocarbon compound having 4 carbon atoms was fed into the feed side of the separating membrane at a temperature of 60° C., while maintaining the opposite (delivery) side of the separating membrane (hollow spaces of the hollow filaments) under a reduced pressure of 3 Torr or less, to allow methyl alcohol to selectively permeate, in the state of a vapor, the separating membrane.

The permeation rate of kg/m²·hr of methyl alcohol through the separating membrane was determined in accordance with the equation:

$$Q_{CH_3OH} = \frac{A_{CH_3OH}}{B}$$

wherein $Q_{CH_3OH}$ represents the permeation rate in kg/m²·hr of methyl alcohol through the separating membrane, $A_{CH_3OH}$ represents an amount in kg of methyl alcohol permeating the separating membrane per hour, and B represents the permeation area in m² of the separating membrane.

The permeation rate of the permeated fraction through the separating membrane was determined in accordance with the equation:

$$Q_{total} = \frac{A_{total}}{B}$$

wherein $Q_{total}$ represents the permeation rate in kg/m²·hr of the permeated fraction through the separating membrane, $A_{total}$ represents an amount of, in kg, the permeated fraction through the separating membrane per hour, and B is as defined above.

The separation factor of the separating membrane with respect to methyl alcohol and the $C_4$ hydrocarbon compound is determined in accordance with the equation:

$$\alpha[CH_3OH/C_4] = \frac{C_1[CH_3OH/C_4]}{C_2[CH_3OH/C_4]}$$

wherein $\alpha[CH_3OH/C_4]$ represents the separation factor of the separating membrane with respect to methyl alcohol and the $C_4$ hydrocarbon compound, $C_1[CH_3OH/C_4]$ represents a proportion in weight of methyl alcohol contained in the permeated fraction to the $C_4$ hydrocarbon compound contained in the permeated fraction, and $C_2[CH_3OH/C_4]$ represents a proportion in weight of methyl alcohol to the $C_4$ hydrocarbon compound contained in the feed mixture.

Example 1

A process system as indicated in FIG. 1 was employed.

A flow ① of methyl alcohol was continuously introduced into a reaction column 1 at a feed rate of 9.69 kg/hr through a conduit 2 and simultaneously a flow ② of a $C_4$ petroleum fraction containing 45%, by weight of isobutylene was continuously introduced into the reaction column 1 at a feed rate of 36.90 kg/hr through a conduit 3. The composition and flow rate of the flow ① through the conduit 2 are indicated in Table 1. Also, the composition and flow rate of the flow ② through the conduit 3 are indicated in Table 1.

In the reaction column 1, methyl alcohol is reacted with isobutylene in liquid phase at a temperature of 67° C. under a pressure of about 10 kg/cm² G in the presence of a catalyst consisting of a strong acid ion-exchange resin to provide methyl-tert-butylether (MTBE). A flow ③ of the resultant reaction product mixture comprising the resultant MTBE, non-reacted portions of methyl alcohol and $C_4$ fraction was fed to a distillation column 4 through a conduit 5. The reaction product mixture flow ③ had the composition and the flow rate as shown in Table 1.

The reaction product mixture was subjected to a distillation at a temperature of 70° C. under a pressure of 14 kg/cm² G to provide a bottom liquid fraction comprising, as the major component thereof, methyl-tert-butylether and a top vapor fraction comprising, as the major components thereof, the non-reacted methyl alcohol and $C_4$ fraction.

The top vapor fraction was withdrawn through the top outlet 11 of the distillation column 4 and conduit 12 and liquefied by the cooler 13. The flow ④ of the liquefied top fraction was fed to the separating membrane module 14 through the conduit 15.

The bottom liquid fraction was recovered through the bottom outlet 7, conduit 8 and cooler 9.

The flow ④ of the liquefied top fraction and the flow ⑤ of the bottom liquid fraction had the compositions and the flow rates as shown in Table 1.

The separating membrane module 14 had an effective membrane area of 11 m². The liquefied top fraction was fed to the feed side of the separating membrane at a temperature of about 60° C. under ambient atmospheric pressure, while maintaining the opposite (delivery) side of the separating membrane under a reduced pressure of 40 Torr.

In this pervaporation procedure, a fraction comprising, as the major component thereof, methyl alcohol permeated, in the state of a vapor, the separating membrane. The permeated vapor fraction comprising, as the major component thereof, methyl alcohol was collected from the separating membrane module 14 and liquefied by the cooler 18. The flow ⑦ of the liquefied fraction had the composition as shown in Table 1 and was returned at a flow rate of 0.81 kg/hr as shown in Table 1 to the reaction column 1.

The non-permeated fraction comprising, as the major component thereof, was withdrawn from the feed side of the separating membrane through the conduit 19. The flow ⑥ of the non-permeated fraction had the composition and the flow rate as shown in Table 1.

The separating membrane module 14 contained a plurality of aromatic polyimide hollow filaments as separating membranes.

The aromatic polyimide was a polymerization product of an aromatic tetracarboxylic acid component consisting of 100 molar % of 3,3',4,4'-biphenyltetracarboxylic dianhydride with an aromatic diamine component consisting of 90 molar % of 2,8-dimethyl-3,7-diaminodibenzothiophene-5,5-dioxide and 10 molar % of 4,4'-diaminodiphenylether, in an equimolar amount to the acid component.

The aromatic polyimide was converted to asymmetric hollow filaments each having a dense layer located on the outside surface of the hollow filament and a porous layer located on the inside surface of the hollow filament.

The resultant aromatic polyimide hollow filaments were subjected to the above-mentioned tests. The follow filaments exhibited a permeation rate of the permeated fraction $Q_{total}$ of about 0.60 kg/m²·hr, and a permeation rate of methyl alcohol $Q_{CH_3OH}$ of about 0.592 kg/m²·hr and had a separation factor $\alpha[CH_3OH/C_4]$ with respect to methyl alcohol and a $C_4$ petroleum fraction of 1400.

TABLE 1

| Item | | ① Flow | ② | ③ | ④ | ⑤ | ⑥ | ⑦ |
|---|---|---|---|---|---|---|---|---|
| Temperature (°C.) | | 67 | 67 | 49 | 60 | 37 | 60 | 67 |
| Composition (wt %) | MTBE | 0.0 | 0.0 | 53.84 | 0.00 | 98.60 | 0.00 | 0.00 |
| | CH₃OH | 100.0 | 0.0 | 2.50 | 4.07 | 1.20 | 0.50 | 95.70 |
| | C₄ hydrocarbon mixture | 0.0 | 100.0 | 43.66 | 95.93 | 0.20 | 99.50 | 4.30 |
| Flow rate (kg/hr) | | 9.69 | 36.90 | 47.40 | 21.52 | 25.88 | 20.54 | 0.81 |

Note:
① Methyl alcohol feed (fresh)
② C₄ hydrocarbon feed (fresh)
③ Reaction product mixture from reaction column
④ Liquefied top fraction from distillation column
⑤ Bottom liquid fraction from distillation column
⑥ Non-permeated fraction from separating membrane module
⑦ Permeated, liquefied fraction from separating membrane module

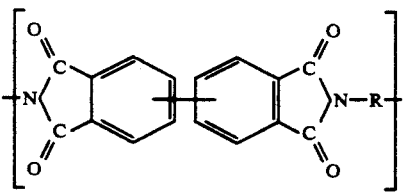

[I]

and

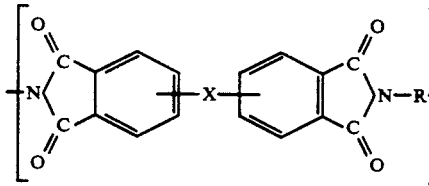

[II]

We claim:

1. A process for continuously producing an ether compound comprising the steps of:

subjecting a lower alcohol having 1 to 3 carbon atoms to a reaction procedure with a hydrocarbon mixture consisting of hydrocarbon compounds having 3 to 6 carbon atoms and comprising, as the major component thereof, an unsaturated hydrocarbon compound having 4 or 5 carbon atoms, to provide a reaction product mixture comprising a resultant ether compound, a non-reacted portion of the lower alcohol and a non-reacted portion of the hydrocarbon mixture;

feeding the resultant reaction product mixture to a distillation procedure in a distillation column, to provide a bottom liquid fraction comprising the resultant ether compound and a top vapor fraction comprising the non-reacted lower alcohol portion and the non-reacted hydrocarbon mixture portion;

collecting the bottom liquid fraction through a bottom outlet of the distillation column;

discharging the top vapor fraction through a top outlet of the distillation column;

liquefying the top vapor fraction by cooling;

bringing the liquefied top fraction into contact with one side face of an aromatic polyimide asymmetric separating membrane having a separation factor, as defined below, of 200 or more, at a temperature of 50° C. or more, while exposing the opposite side face of the separating membrane to an atmosphere maintained under reduced pressure, to allow a vapor fraction comprising, as a major component thereof, the non-reacted lower alcohol to selectively permeate the separating membrane, said aromatic polyimide in the asymmetric separating membrane comprises 70 to 100 molar % of at least one type of recurring unit selected from those of the formulae (I) and (II):

wherein R represents a divalent aromatic group having 2 to 4 benzene ring structures and X represents a member selected from the group consisting of —S—, —SO₂—, —CO— —O—, —C(CH₃)₂—, —CH₂—, and C(CF₃)₂— groups, and said separation factor being determined in accordance with the equation:

$\alpha = C_1/C_2$ wherein $\alpha$ represents the separation factor of the separating membrane, $C_1$ represents a proportion in weight of the non-reacted lower alcohol contained in the permeated fraction and $C_2$ represents a proportion in weight of the non-reacted lower alcohol contained in the liquefied top fraction to the non-reacted hydrocarbon mixture contained in the liquified top fraction;

cooling the permeated lower alcohol vapor fraction to liquefy and collect the same;

returning the liquefied lower alcohol fraction to the reaction step.

2. The process as claimed in claim 1, wherein the lower alcohol is selected from the group consisting of methyl alcohol, ethyl alcohol and propyl alcohol.

3. The process as claimed in claim 1, wherein the unsaturated hydrocarbon compound having 4 or 5 carbon atoms is selected from the group consisting of isobutylene, 2-methyl-2-butene, and 2-methyl-1-butene.

4. The process as claimed in claim 1, wherein the hydrocarbon mixture comprises the unsatuated hydrocarbon compound having 4 to 5 carbon atoms in an amount of 30 to 100% based on the total weight of the hydrocarbon mixture.

5. The process as claimed in claim 1, wherein the reaction procedure of the lower alcohol with the unsaturated hydrocarbon compound is carried out in a liquid phase at a temperature of 30° C. to 100° C. under a pressure of 5 to 30 kg/cm² G.

6. The process as claimed in claim 1, wherein the reaction procedure of the lower alcohol with the hydrocarbon mixture is carried out in the presence of a catalyst comprising a strong acid ion-exchange resin.

7. The process as claimed in claim 1, wherein the resultant reaction product mixture in the reaction step comprises 20 to 70% by weight of the resultant ether compound, 0.5 to 10% by weight of the non-reacted lower alcohol portion and 25 to 80% by weight of the non-reacted hydrocarbon mixture portion.

8. The process as claimed in claim 1, wherein the aromatic polyimide is solvent-soluble and comprises a polymerization product of:
  (A) an aromatic tetracarboxylic acid component comprising:
    (a) 70 to 100 molar % of at least one principal aromatic tetracarboxylic acid compound selected from the group consisting of biphenyltetracarboxylic acids, diphenylether tetracarboxylic acids, benzophenone tetracarboxylic acids, diphenylsulfone tetracarboxylic acids, diphenylpropane tetracarboxilic acids, diphenylthioether tetracarboxylic acids, diphenylhexafluoropropane tetracarboxylic acids and dianhydrides, esters and salts of the above-mentioned acids, and
    (b) 0 to 30 molar % of at least one additional aromatic tetracarboxylic acid compound selected from the group consisting of aromatic tetracarboxylic acids different from the above-mentioned principal aromatic tetracarboxylic acids (a), dianhydrides, esters and salts of the above-mentioned acids; with
  (B) an aromatic diamine components comprising:
    (c) 70 to 100 molar % of at least one principal aromatic diamine compound having a 2 to 4 benzene ring structure, and
    (d) 0 to 30 molar % of at least one additional aromatic diamine compound different from the above-mentioned principal aromatic diamine compound (c).

9. The process as claimed in claim 8, wherein the principal aromatic tetracarboxylic acid compound (a) is selected from the group consisting of 2,3,3',4'-biphenyltetracarboxylic acid, 3,3',4,4'-biphenyltetracarboxylic acid, 3,3',4,4'-diphenylethertetracarboxylic acid, 3,3',4,4'-benzophenonetetracarboxylic acid, 3,3',4,4'-diphenylthioether tetracarboxylic acid, 3,3',4,4'-diphenylsulfonetetracarboxylic acid, 2,2-bis(3,4-carboxyphenyl)propane, and 2,2-bis(3,4-carboxyphenyl)hexafluoropropane, and dianhydrides, acid chlorides and lower alkyl esters of the above-mentioned acids.

10. The process as claimed in claim 8, wherein the principal aromatic diamine compounds (c) is selected from the group consisting of diaminodiphenylethers, diaminodiphenyl-thioethers, diaminodiphenylsulfones, diaminodiphenylmethanes, diaminodiphenyl propanes, diaminodibenzothiophenes, diaminodiphenylenesulfones, diaminoethioxanthones, diaminoethioxanthenes, bis(aminophenoxy)benzenes, di(aminophenyl)benzenes, di[(aminophenoxy)phenyl]alkanes, di[(aminophenoxy)phenyl]sulfones, di(aminophenoxy)biphenyls and 9,10-(diaminophenyl)anthracene compounds.

11. The process as claimed in claim 1, wherein the aromatic polyimide asymmetric separating membrane is in the form of a hollow filament or a flat film.

12. The process as claimed in claim 1, wherein the aromatic polyimide asymmetric separating membrane has a dense layer having a thickness of 0.001 to 5 μm and a porous layer having a thickness of 10 to 2,000 μm and continues from the dense layer in the direction of the thickness of the membrane.

13. The process as claimed in claim 1, wherein the contact of the liquefied top fraction with one side face of the aromatic polyimide asymmetric separating membrane is carried out under a pressure of from ambient atmospheric pressure to 20 kg/cm².

14. The process as claimed in claim 1, wherein the reduced pressure on the opposite side of separating membrane is 200 Torr or less.

15. The process as claimed in claim 1, wherein the ether compound is selected from the group consisting of methyl-tert-butyl ether, 2-ethoxy-2-methylpropane, 2-propoxy-2-methylpropane, 2-methoxy-2-methylbutane, and 2-ethoxy-2-methylbutane.

* * * * *